United States Patent [19]
Stelling et al.

[11] 4,212,845
[45] Jul. 15, 1980

[54] ANALYTICAL APPARATUS

[75] Inventors: David Stelling, Broadstairs; David H. Barker, Birchington; Terence E. Weston, Herne Bay, all of England

[73] Assignee: The Rank Organisation Limited, London, England

[21] Appl. No.: 922,109

[22] Filed: Jul. 5, 1978

[30] Foreign Application Priority Data

Jul. 6, 1977 [GB] United Kingdom ............... 28286/77

[51] Int. Cl.² .......................... G01N 1/10; G01N 1/14; G01N 1/18
[52] U.S. Cl. ...................................... 422/82; 422/101; 210/65
[58] Field of Search ................................ 422/82, 101; 73/421.5 R, 425.4 R; 210/65

[56] References Cited
U.S. PATENT DOCUMENTS

| | | | |
|---|---|---|---|
| 2,967,764 | 1/1961 | Skeggs | 422/82 |
| 3,109,713 | 11/1963 | Ferrari et al. | 422/82 |
| 3,435,684 | 4/1969 | Smythe | 422/82 |
| 3,479,141 | 11/1969 | Smythe et al. | 422/82 |
| 3,600,953 | 8/1971 | Isreeli | 422/82 X |
| 3,627,495 | 12/1971 | Adler, Jr. et al. | 422/82 |
| 3,640,822 | 2/1972 | Hrdina | 422/82 |

Primary Examiner—R. E. Serwin
Attorney, Agent, or Firm—Brisebois & Kruger

[57] ABSTRACT

Apparatus for separating a stream of flowing liquid in a conduit into segments separated by gas bubbles of a known or at least controllable size includes a chamber communicating with the interior of the conduit and a duct of smaller cross section than the chamber, which projects into the chamber and is connectable to a source of gas under pressure: the size of the gas chamber, can be adjusted to change the rate at which the gas bubbles are injected and thus vary the length of the liquid segments.

11 Claims, 2 Drawing Figures

ANALYTICAL APPARATUS

The present invention relates to analytical apparatus and particularly to apparatus constructed for the performance of the so-called continuous flow analysis.

Continuous flow analysis is performed on liquids by directing them along a conduit, the flowing liquid stream being segmented with gas bubbles. This has particular advantages in reducing mixing and turbulent flow in the flowing stream which might cause modification to a reaction the progress of which is to be monitored by the analysis. It is important for such apparatus to be able to introduce the segmenting gas bubbles in a regular and controlled way, and known such continuous flow analysers operate to introduce gas segments or bubbles into the system from a peristaltic pump. However, the frequency and size of the gas segments or bubbles produced in this way was not sufficiently regular and accurate for the purposes of the analysis. This is particularly important with modern high speed high precision analysis apparatus. In order to overcome this problem attempts have been made to introduce the gas segment into the liquid stream by using an attachment to a peristaltic pump called an "air bar", which operates in such a way that the gas segment is allowed to be introduced when each roller of the peristaltic pump leaves the head; the air bar compresses the gas tube after it has passed through the pump proper, and is actuated by the pump drive. The disadvantages of this device are that there are no adjustments to allow for small variations which may be due, for example, to differences in pump tube pumping rate from batch to batch. Nor is it possible to vary the size of the gas segments introduced by the device and the particular kind of tubing, silicone tubing, used in the device is prone to stick with the continual action of the bar.

The present invention seeks, therefore, to provide a device for separating a stream of liquid in a conduit into segments in which the gas segemnts introduced into the liquid may be of uniform size and frequency. The present invention also seeks to provide apparatus for separating a stream of liquid into segments in which the gas segments can be adjusted with respect to size and frequency. It is important that a constantly accurate separation of the liquid stream into segments is achieved with a variety of flow rates of liquid stream and back pressures from the analytical system.

Accoring to the present invention apparatus for separating a stream of liquid in a conduit into segments by the introduction of gas bubbles comprises, a chamber communicating with the conduit at one side thereof and a duct of smaller cross section that that of the opening communicating with the chamber and being connectable to a source of gas under pressure such that, in use of the apparatus, when a stream of liquid is flowing in the conduit, gas can be introduced through the duct into the chamber at a controlled rate, the gas pressure increasing in the chamber until it overcomes the surface tension of the liquid and the pressure therein and a bubble of gas enters the stream of liquid. Immediately after a bubble of gas has entered the liquid stream the gas pressure in the chamber falls to approximately the same as the pressure in the liquid stream and the process is repeated. In order to obtain accurate regularity of the segmentation of the flowing liquid stream, therefore, it is only necessary to maintain constant the flow of gas through the duct, and this latter can be achieved fairly readily.

Preferably, the chamber is adjustable in size whereby to adjust the rate at which gas bubbles are introduced into the liquid stream in the conduit. The rate at which bubbles are introduced into the liquid stream and the conduit may also be adjusted by varying the rate at which gas is delivered to the chamber through the duct. However, for a given flowrate through the duct, an adjustment in the size of the chamber will have the same effect since the volume of the chamber will determine the time taken for the pressure in the chamber to reach the critical pressure at which a gas bubble breaks away into the liquid stream in the conduit.

In a preferred embodiment of the invention the chamber is generally cylindrical and within it is located a gas injector comprising a cylindrical body which is a sliding fit within the chamber, the duct being a passage within the injector body opening into the end face thereof in communication with the chamber. The injector body is preferably simply a tube and the passage is the hollow interior thereof extending axially of the tube.

The conduit and the chamber may be formed separately, for example by joining two tubes together in a T-configuration, or may be formed as communicating passages in a common body.

In a preferred embodiment of the invention in which the conduit and the chamber are formed as communicating passages in a common body, the gas injector is resiliently biased away from the chamber and supported in a carrier which is screwed into the threaded hole in the body. For practical simplicity the gas injector is located in the carrier, in this embodiment, by a collar fixed to the injector, which collar abuts a shoulder in the carrier, the resilient bias being applied by a spring which also urges a sealing ring against a cooperating surface of the body to seal the chamber. The threaded hole is, of course, of greater diameter than the chamber since the injector body which is substantially the same diameter as the chamber is carried within a carrier which is screwed into the threaded hole. The chamber therefore communicates with the threaded hole via a connecting section having a conical surface and this conical surface preferably constitutes the said cooperating surface against which the sealing ring is pressed to seal the chamber, pressure from the spring being applied to the sealing ring by a sliding collar surrounding the gas injector and interposed between the end of the spring and the sealing ring.

Two embodiments of the present invention will now be more particularly described, by way of example, with reference to the accompanying drawings, in which.

Figure 1:
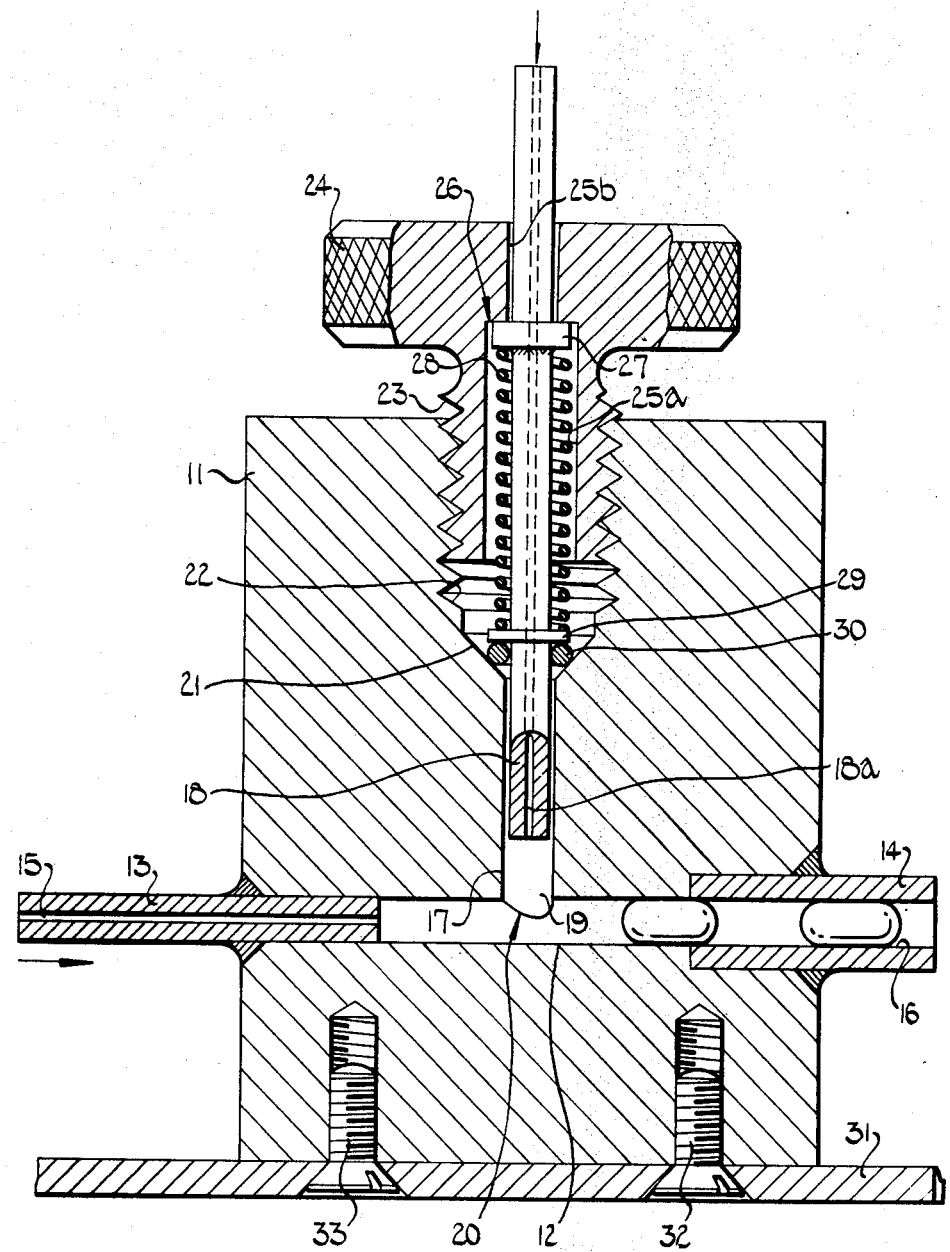
FIG. 1 is a schematic cross sectional view of a first embodiment.

Referring first to FIG. 1, the embodiment shown comprises a body 11 through which passes a passageway 12 constituting the conduit along which flows the liquid stream. The tube 13 the outer diameter of which is equal to the diameter of the conduit 12 is inserted into one end to form an input connector, and a section of tubing 14 the inner diameter of which is equal to the diameter of the conduit 12 is inserted into a counterbore in the body 11 to form an output connector. The tube 13 has a bore 15 of smaller dimension than the conduit 12, and the tubing 14 has a bore 16 of substantially the same dimension of the conduit 12.

Extending transversely with respect to the conduit 12 is a second passage 17 of substantially the same diameter as the conduit 12, which passage, together with a tube 18 having a narrow bore 18a, defines a gas chamber 19 which communicates with the conduit 12 via an opening schematically indicated 20.

The passage 17 communicates via a conical section 21 with a threaded hole 22 in which is threadedly engaged a carrier body 23 having a knurled enlarged end 24 by means of which the carrier body 23 can be screwed into or out from the threaded hole 22.

Within the carrier 23 there is an axial bore 25 formed in two parts, a first part 25a of larger diameter and a second part 25b of smaller diameter, the two parts meeting at a shoulder 26 against which abuts a collar 27 which is fixed securely to the tube 18 which constitutes the gas injector.

A coil spring 28 surrounds the tube 18 and one end presses against the fixed collar 27; the other end of the spring 28 presses against a sliding collar 29 which abuts against a sealing ring 30 which is trapped between the sliding collar 29 and the conical section 21 linking the cylindrical passage 17 with the threaded hole 22. The spring 28 serves, at the same time, to bias the sliding collar 29 towards the gas chamber 19 to press the sealing ring 30 against the conical section 21 to seal the gas chamber 19, and to bias the gas injector 18, via the fixed collar 27, away from the gas chamber 19, the fixed collar 27 being pressed by the spring 28 against the shoulder 26. Adjustments to the carrier 23 by turning the knurled finger grip 24 thus displaces the gas injector 18 towards the conduit 12 thereby reducing the volume of the gas chamber 19, or (upon turning the carrier 23 in the opposite direction) permits the gas injector 18 to be displaced by the spring 28 away from the gas chamber 19 thereby enlarging the latter.

The body 11 may, for example, be a plastics block and methyl methacrylate (RTM Perspex) has been found to be particularly suitable. The body 11 is shown secured to a support plate 31 by two countersunk screws 32, 33 although other fixings may, of course, be utilised if desired.

In use of the apparatus a liquid to segmented is introduced into the conduit 12 through the bore 15 in the tube 13 and a gas under pressure which is to form the segmenting bubbles is introduced into the gas chamber 19 through the bore 18a and the gas injector 18. The pressure in the gas chamber 19 increases and, as can be seen in the drawing, the lower boundary of the gas chamber projects into the flowing stream by an ever increasing amount until the pressure in the flowing stream and the surface tension of the liquid are overcome and a gas bubble detached itself from the gas chamber 19 and enters the conduit 12. The pressure in the gas chamber 19 then falls to substantially that of the liquid in the conduit 12, but slowly builds up as more gas flows in through the passage 18a in the gas injector 18 until a further bubble is injected into the flowing stream in the conduit 12. Minor variations in the gas flowrate due to variations in the pump supplying the gas, or to variations in the diameter of the bore 18a, can be accommodated by adjusting the carrier 23 to adjust the size of the gas chamber 19. By making the gas chamber 19 a relatively long cylindrical chamber large adjustments to its volume can be made by adjusting the carrier 23 so that quite substantial adjustments to the rate at which gas bubbles are introduced into the liquid stream in the conduit 12 can be made. Of course such adjustments can also be made by varying the rate at which gas is introduced into the chamber 19 through the passage 18a in the gas injector 18.

The natural length of the coil spring 28 should be such that it still applies an adequate pressure to the sealing ring 30 even when the carrier 23 is withdrawn from the hole 22 by its maximum amount to enlarge the gas chamber 19 to its fullest extent. If the volume of the chamber 19 is increased in this way, the gas, for a given flow rate in the injector 18, will take longer to reach a sufficient pressure to overcome the liquid pressure and therefore the rate of production of gas segments in the liquid stream in the conduit 12 will be slower.

Figure 2:
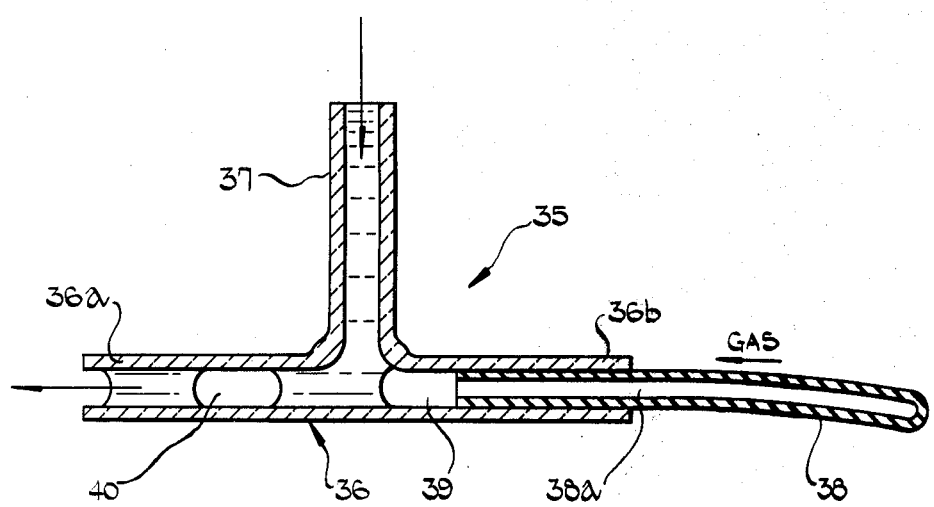
FIG. 2 is a cross sectional view of a second embodiment.

In the embodiment of FIG. 2 the conduit is formed by two separate pipes joined together to form a T-piece generally indicated 35 and having a crosspiece 36 with two arms 36a and 36b, and an upright 37.

A length of flexible (e.g. rubber) tube 38 is fitted into one arm, in this case the arm 36b of the crosspiece 36 to form an injector for the gas and to define a gas chamber 39 between its end and the junction of the crosspiece 36 with the upright 37. The interior 38a of the tube 38 constitutes the above mentioned duct.

In use of the device liquid flows into the T-piece through the upright arm 37 and a gas pressure in the chamber 39 is maintained by feeding gas in through the tube 38. The size of the gas chamber 39 can be adjusted simply, but not very accurately, by adjusting the position of the tube 38 in the arm 36b of the crosspiece 36, pushing it in further to reduce the size of the gas chamber 39 and easing it further out to increase the gas chamber size.

What is claimed is:

1. In a continuous flow analyser wherein a stream of liquid is divided prior to analysis into segments by the introduction of gas bubbles, apparatus for effecting said division of the liquid stream, said apparatus comprising
   means defining a conduit along which the liquid stream can flow
   means defining a chamber communicating with said conduit at one side thereof, and
   means defining a duct of smaller cross section than that of said chamber, said duct communicating with said chamber and being connectable to a source of gas under pressure such that, in use of the apparatus, when a stream of liquid is flowing in said conduit, gas can be introduced through said duct into said chamber at a controlled rate, the gas pressure increasing in the chamber until it overcomes the surface tension of the liquid and the pressure therein and a bubble of gas enters the stream of liquid.

2. Apparatus as in claim 1, wherein said chamber is adjustable in size whereby to adjust the rate at which gas bubbles are introduced into the liquid stream in said conduit.

3. Apparatus as in claim 1 or claim 2, wherein said chamber is generally cylindrical,
   a gas injector located within said chamber, said gas injector comprising a cylindrical body which is a sliding fit within said chamber, said duct being a passage within said cylindrical injector body, said duct opening into the end face of said cylindrical injector body and communicating with said chamber.

4. Apparatus as in claim 3, wherein said injector body is a tube and said passage extends axially thereof.

5. Apparatus as in claim 1, wherein said conduit and said chamber are formed as communicating passages in common body.

6. Apparatus as in claim 5, wherein there are resilient biasing means biasing said gas injector away from said chamber, carrier means supporting said gas injector, and means defining a threaded hole in said body, said carrier means being screwed into said threaded hole.

7. Apparatus as in claim 6, wherein said carrier has an internal shoulder, said injector has a collar and is located in said carried by said collar abutting said shoulder in said carrier, said resilient biasing means being constituted by a spring which also urges a sealing ring against a co-operating surface of said body to seal said chamber.

8. Apparatus as in claim 7, wherein said chamber communicates with said threaded hole via a connecting section having a conical surface which constitutes said cooperating surface against which said sealing ring is pressed.

9. Apparatus as in claim 8, wherein there is further provided a sliding collar surrounding said gas injector and interposed between the end of said spring and said sealing ring.

10. Apparatus in any of claims 1 to 5, wherein said conduit and said chamber are defined by two tubes connected together in a T-configuration.

11. Apparatus as in claim 10, wherein said injector is a resilient tube inserted into one arm of said T-piece and adjustable therealong to determine the size of said chamber.

* * * * *